(12) United States Patent
Canada et al.

(10) Patent No.: US 8,021,685 B2
(45) Date of Patent: Sep. 20, 2011

(54) WOUND CARE DEVICE HAVING FLUID TRANSFER PROPERTIES

(75) Inventors: T. Andrew Canada, Campobello, SC (US); Martin E. Cowan, Moore, SC (US); Kenneth M. Wiencek, Inman, SC (US)

(73) Assignee: Milliken + Co, Spartanburg, SC (US)

( * ) Notice: Subject to any disclaimer, the term of this patent is extended or adjusted under 35 U.S.C. 154(b) by 0 days.

(21) Appl. No.: 12/908,126

(22) Filed: Oct. 20, 2010

(65) Prior Publication Data

US 2011/0040289 A1    Feb. 17, 2011

Related U.S. Application Data

(60) Division of application No. 11/347,522, filed on Feb. 3, 2006, now Pat. No. 7,842,306, which is a continuation-in-part of application No. 10/640,837, filed on Aug. 14, 2003, now abandoned, and a continuation-in-part of application No. 10/640,918, filed on Aug. 14, 2003, and a continuation-in-part of application No. 10/640,919, filed on Aug. 14, 2003, and a continuation-in-part of application No. 11/068,639, filed on Feb. 28, 2005.

(51) Int. Cl.
*A61K 33/42* (2006.01)

(52) U.S. Cl. .................. 424/445; 424/604; 442/123

(58) Field of Classification Search .................. None
See application file for complete search history.

(56) References Cited

U.S. PATENT DOCUMENTS

| | | | |
|---|---|---|---|
| 3,930,000 A | 12/1975 | Margraf | 424/245 |
| 4,728,323 A | 3/1988 | Matson | 604/304 |
| 5,009,652 A | 4/1991 | Morgan et al. | 604/385 |
| 5,019,096 A | 5/1991 | Fox, Jr. et al. | 623/1 |
| 5,147,338 A | 9/1992 | Lang et al. | 604/304 |
| 5,296,518 A | 3/1994 | Grasel et al. | 521/176 |
| 5,409,472 A | 4/1995 | Rawlings et al. | 604/307 |
| 5,571,079 A | 11/1996 | Bello et al. | 602/46 |
| 5,607,683 A | 3/1997 | Capelli | 424/405 |
| 5,662,913 A | 9/1997 | Capelli | 424/405 |
| 5,744,151 A | 4/1998 | Capelli | 424/405 |
| 5,782,787 A | 7/1998 | Webster | 602/46 |
| 5,810,755 A | 9/1998 | LeVeen et al. | 602/48 |
| 5,899,785 A | 5/1999 | Groten et al. | 442/334 |
| 5,914,125 A | 6/1999 | Andrews et al. | 424/443 |
| 5,970,583 A | 10/1999 | Groten et al. | 19/296 |
| 5,973,221 A | 10/1999 | Collyer et al. | 602/46 |
| 6,019,996 A | 2/2000 | Cheong | 424/445 |
| 6,071,447 A | 6/2000 | Bootman et al. | 264/54 |
| 6,087,549 A | 7/2000 | Flick | 602/41 |
| 6,093,414 A | 7/2000 | Capelli | 424/405 |
| 6,143,318 A | 11/2000 | Gilchrist et al. | 424/446 |
| 6,153,215 A | 11/2000 | Samuelsen et al. | 424/448 |
| 6,160,196 A | 12/2000 | Knieler et al. | 602/48 |
| 6,194,332 B1 | 2/2001 | Rock et al. | 443/312 |
| 6,326,410 B1 | 12/2001 | Cheong | 521/67 |
| 6,333,093 B1 | 12/2001 | Burrell et al. | 428/194 |
| 6,399,091 B1 | 6/2002 | Berthold et al. | 424/443 |
| 6,468,521 B1 | 10/2002 | Pedersen et al. | 424/78.17 |
| 6,548,727 B1 | 4/2003 | Swenson | 602/41 |
| 6,584,668 B2 | 7/2003 | Green et al. | 29/527.2 |
| 6,821,936 B2 | 11/2004 | Green et al. | 510/319 |
| 6,946,433 B2 | 9/2005 | Green et al. | 510/310 |
| 2002/0172709 A1 | 11/2002 | Nielsen et al. | 424/445 |
| 2002/0187175 A1 | 12/2002 | Petrea et al. | 424/404 |
| 2003/0021832 A1 | 1/2003 | Scherr | 424/445 |
| 2004/0001880 A1 | 1/2004 | Bowler et al. | 424/442 |
| 2004/0106340 A1 | 6/2004 | Kreider et al. | 442/59 |
| 2004/0106341 A1 | 6/2004 | Vogt et al. | 442/59 |
| 2005/0035327 A1 | 2/2005 | Canada et al. | 424/404 |
| 2005/0037057 A1 | 2/2005 | Schuette et al. | 424/443 |

FOREIGN PATENT DOCUMENTS

| | | | |
|---|---|---|---|
| DE | 155 873 | 7/1982 | 3/51 |
| EP | 0 242 415 | 8/1986 | 8/77 |
| GB | 2 321 216 | 7/1998 | |
| WO | WO 02/36866 A1 | 11/2001 | |
| WO | WO 02/62403 A1 | 2/2002 | |
| WO | WO 02/78755 A2 | 3/2002 | |
| WO | WO 03/043553 A1 | 5/2003 | |
| WO | WO 2005/018543 | 3/2005 | |
| WO | WO 2006/036581 | 4/2006 | |

OTHER PUBLICATIONS

International Search Report PCT/US2006/007368.

*Primary Examiner* — Robert A Wax
*Assistant Examiner* — Hasan Ahmed
(74) *Attorney, Agent, or Firm* — Brenda D Wentz

(57) ABSTRACT

This disclosure relates to wound care devices which are capable of one-way, directional flow of fluids and contaminants away from the wound site to the opposite side of the wound care device, which functions as a fluid reservoir. This fluid transport mechanism generally aids in reducing wound maceration by removing excess fluid, and potentially even bacteria, and is carried out without loss of physical integrity of the wound care device itself. In addition to providing a uni-directional fluid transport mechanism, the wound care device may contain a topically applied silver-based antimicrobial finish which provides certain levels of antimicrobial agent to the wound in order to clear infection from the wound site and control bacterial growth in the wound care dressing. Exemplary topical antimicrobial finishes include silver ion-releasing compounds.

2 Claims, No Drawings

WOUND CARE DEVICE HAVING FLUID TRANSFER PROPERTIES

CROSS-REFERENCE TO RELATED APPLICATIONS

This application is a divisional of U.S. patent application Ser. No. 11/347,522, entitled "Wound Care Device Having Fluid Transfer Properties," which was filed on Feb. 3, 2006, now U.S. Pat. No. 7,842,306 which is a continuation-in-part of U.S. patent application Ser. No. 10/640,837, entitled "Topical Silver-Based Antimicrobial Composition for Wound Care Devices," which was filed on Aug. 14, 2003, now abandoned U.S. patent application Ser. No. 10/640,918, entitled "Silver-Containing Wound Care Device," which was filed on Aug. 14, 2003, U.S. patent application Ser. No. 10/640,919, entitled "Method for Producing a Silver-Containing Wound Care Device," which was filed on Aug. 14, 2003, and U.S. patent application Ser. No. 11/068,639, entitled, "White Silver-Containing Wound Care Device," which was filed on Feb. 28, 2005.

TECHNICAL FIELD

This disclosure relates to a wound care device which contains capillary force one-way pumps that are capable of transporting fluid, such as wound exudate, away from a wound site to the opposite side of the wound care device, which functions as a segregated fluid reservoir. This fluid transport mechanism generally aids in reducing wound maceration by removing excess wound fluid and the protease enzymes and infectious bacteria contained within the wound fluid. The wound care device performs this function, often times for multiple days, without the loss of the physical integrity of the wound care device. In addition to providing a uni-directional fluid transport mechanism, the wound care device may contain a topically applied silver-based antimicrobial finish which provides certain levels of antimicrobial agent to the wound in order to reduce infection from the wound site and control microbial growth in the wound care dressing. Exemplary topical antimicrobial finishes include silver ion-releasing compounds.

In one potentially preferred embodiment, the wound care device is comprised of a knit construction characterized in that polyester fiber is primarily present on the wound contact surface and nylon fiber is primarily present on the fluid reservoir surface. A third fiber, such as an elastomeric polyurethane known by the tradename Lycra®, may also be included in order to provide some amount of elasticity to the wound care device. The wound care device provides a one way directional flow of fluid away from the wound and into the nylon fluid reservoir. Since the fluid is partitioned away from the wound, the propensity of localized wound maceration is reduced. Furthermore, due to the construction of the wound care device, at least in part, the device maintains a high degree of physical integrity when saturated with fluid.

BACKGROUND

In the medical field, and in the area of wound care particularly, it is well-established that many factors, including the amount of moisture present at a wound site, affects how quickly a wound will heal. Generally speaking, having an excessive amount of moisture present at a wound site, especially when combined with the warm environment provided by the body, leads to undesirable bacteria growth and production of protease enzymes in the wound. Such growth can cause further damage to healthy cells and delay the healing process. However, insufficient moisture at the wound site can cause eschar (scab) formation and scarring and may cause the wound care device, or medical dressing, to adhere to the wound. If the dressing adheres to the wound, subsequent removal of the dressing may cause undue discomfort to the patient as well as disrupt newly granulated tissue. Infection of the wound may also be compounded when a medical dressing is removed and portions of the dressing remain behind in the wound itself, particularly if the dressing is already colonized with pathogenic microbes. Thus, it is important that the dressing maintains its physical integrity when exposed to stress, such as during removal from the wound, in order to prevent additional complications and delays in healing.

Absorptive materials such as gauzes, hydrogels, swellable fibers, foams, woven textiles and the like have been incorporated into wound care devices for the purpose of controlling the wound moisture content. Fluids are generally absorbed by these types of materials by reversible capillary action or osmosis rather than by a one-way directional flow created by an inventive two-sided wound care device.

For example, U.S. Pat. No. 5,009,652 to Morgan et al. discloses a disposable laminated medical sponge that contains a thin film which is impervious to fluids and infectious agents. The medical sponge is designed to prevent the seepage of bodily fluids from one side of the sponge to the opposite side, since such seepage provides risk of infection for health-care workers having direct contact with patients.

U.S. Pat. No. 6,194,332 to Rock et al. discloses an antimicrobial composite fabric having a first inner fabric layer and a second outer fabric layer. The inner fabric layer may be comprised of polyester, acrylic or nylon fiber which has been rendered hydrophilic, such as by mechanical or chemical treatment. The hydrophilic inner fabric layer enables the transport of sweat from the inner fabric layer to the outer fabric layer. The fibers in the outer layer of the fabric may be blended with antimicrobial fibers in order to reduce the proliferation of bacteria in this layer. The fabric may be formed into a garment which provides reduced body odor. U.S. Pat. No. 6,602,811 to Rock et al. discloses a similar antimicrobial composite fabric, except that the second outer fabric layer also may be treated with an antimicrobial paste.

US Patent Application Publication No. 2004/0001880 to Bowler et al. discloses the use of gel forming fibers such as sodium carboxymethycellulose which can be incorporated into wound dressings. Silver ions may be incorporated into the fibers by combining them in a solution with a solvent prior to fiber formation. The dressing may be used as part of a larger dressing or a layer in a multi-layered dressing and need not be in direct contact with the wound.

The wound care device of the present invention takes advantage of a unique textile fabric construction which effectively isolates fluid away from the wound, which often results in improved healing. The differentiation that exists in a wound care device having a hydrophobic fiber on the wound contact side of the device and hydrophilic fiber on the fluid reservoir side of the device creates a unique one-way, directional flow of fluid and contaminants away from the wound.

A further feature of the wound care device of the present invention is that the device may also contain a topical coating of an antimicrobial agent such as silver. It is known that placing surface-available silver in contact with a wound allows the silver to enter the wound and become absorbed by undesirable bacteria and fungi that grow and prosper in the warm, moist environment of the wound site. Once absorbed, the silver ions kill microbes, resulting in treatment of infected wounds or the prevention of infection in at-risk wounds.

Methods of topically applying a silver-based antimicrobial finish to textile substrates are described, for example, in commonly assigned U.S. Pat. Nos. 6,584,668; 6,821,936; and 6,946,433 and in commonly assigned U.S. patent application Ser. Nos. 09/586,081; 09/589,179; 10/307,027; and 10/306,968. All of these patents and patent applications are hereby incorporated by reference. Details of many of these processes will be discussed below.

The present disclosure addresses and overcomes the problems described above. Whereas, historically, a gauze or foam medical dressing has been applied to a wound with at least some intent on absorbing fluids, the present disclosure describes a wound care device capable of creating a one-way, directional flow of fluid and contaminants away from the wound, without detrimentally causing excessive dryness of the wound and substantial adherence of the device to the wound. The wound care device may additionally provide desired release of silver to the wound site for antimicrobial efficacy and, because of its unique construction, maintains its physical integrity when exposed to stress during ordinary use of the wound care device.

For these reasons and others that will be described herein, the present wound care device having unique fluid management properties represents a useful advance over the prior art.

DETAILED DESCRIPTION

Definitions and Terms

"Hydrophilic" is defined as having a strong affinity for or the ability to absorb water.

"Hydrophobic" is defined as lacking affinity for or the ability to absorb water.

"Non-electrically conductive" is defined as having a resistance in ohms per square inch of fabric of greater than about 10,000 ohms, preferably greater than about 100,000 ohms and most preferably greater than about $1 \times 10^9$ ohms, when measured in accordance with AATCC Test Method 76-1978.

Wound Care Device

The wound care device of the present invention is generally intended to be used for treatment of various wounds including, without limitation, partial thickness burns, incisions, skin grafts, donor sites, lacerations, abrasions, Stage I-IV pressure ulcers, vascular venous stasis, and diabetic ulcers. The wound care device is generally comprised of a fabric formed from synthetic fibers, natural fibers, or combinations thereof.

Synthetic fibers include, for example, polyester, acrylic, polyamide, polyolefin, polyaramid, polyurethane, regenerated cellulose (i.e., rayon), and blends thereof. The term "polyamide" is intended to describe any long-chain polymer having recurring amide groups (—NH—CO—) as an integral part of the polymer chain. Examples of polyamides include nylon 6; nylon 6, 6; nylon 1, 1; and nylon 6, 10. The term "polyester" is intended to describe any long-chain polymer having recurring ester groups (—C(O)—O—). Examples of polyesters include aromatic polyesters, such as polyethylene terephthalate (PET), polybutylene terephthalate (PBT), polytrimethylene terephthalate (PTT), and polytriphenylene terephthalate, and aliphatic polyesters, such as polylactic acid (PLA). "Polyolefin" includes, for example, polypropylene, polyethylene, and combinations thereof. "Polyaramid" includes, for example, poly-p-phenyleneteraphthalamid (i.e., Kevlar®), poly-m-phenyleneteraphthalamid (i.e., Nomex®), and combinations thereof. Natural fibers include, for example, wool, cotton, flax, and blends thereof.

The fabric may be formed from fibers or yarns of any size, including microdenier fibers and yarns (fibers or yarns having less than one denier per filament). The fibers or yarns may have deniers that range from less than about 1 denier per filament to about 2000 denier per filament or more preferably, from less than about 1 denier per filament to about 500 denier per filament, or even more preferably, from less than about 1 denier per filament to about 300 denier per filament.

Furthermore, the fabric may be partially or wholly comprised of multi-component or bi-component fibers or yarns, which may be splittable, or which have been partially or fully split, along their length by chemical or mechanical action. The fabric may be comprised of fibers such as staple fiber, filament fiber, spun fiber, or combinations thereof.

The fabric may be of any variety, including but not limited to, woven fabric, knitted fabric, nonwoven fabric, or combinations thereof. The fabric may optionally be colored by a variety of dyeing techniques, such as high temperature jet dyeing with disperse dyes, vat dyeing, thermosol dyeing, pad dyeing, transfer printing, screen printing, or any other technique that is common in the art for comparable textile products. If yarns or fibers are treated by the process of the current invention, they may be dyed by suitable methods prior to fabric formation, such as, for instance, by package dyeing or solution dyeing, or after fabric formation as described above, or they may be left undyed.

Other additives may be present on and/or within the target fabric or yarn, including antistatic agents, optical brightening compounds, opacifiers (such as titanium dioxide), nucleating agents, antioxidants, UV stabilizers, fillers, permanent press finishes, softeners, lubricants, curing accelerators, adhesives, and the like. The present fabrics may also be coated or printed or otherwise aesthetically modified in addition to being treated with the present antimicrobial compositions. Printing may be achieved, for example, by screenprinting or flexographic printing techniques.

One specific example of a knit pattern that is suitable for making the fabric that comprises the wound care device of the present invention is a jersey knit. A jersey knit is a circular or flat-knit fabric made with a plain stitch in which the loops intermesh in only one direction. As a result, the appearance of the face and the back of the jersey fabric is wholly different. Thus, by utilizing a jersey knit to form a fabric comprised of polyester, nylon, and elastomeric fibers, a fabric may be constructed that is primarily polyester-containing on one side while the opposite side of the fabric is primarily nylon-containing. The elastomeric fiber provides some level of stretch to the fabric, which may be useful for some wounds that require, for example, a dressing to be wrapped snugly around the wound site. The elastomeric fiber, in addition to providing conformability to the wound care device, also provides some level of softness to the device. Spandex is one non-limiting example of an elastomeric fiber and may be known by the tradename Lycra®, which is available from INVISTA of Wichita, Kans.

Additionally, it may be generally known to those skilled in the art that a knit polyester fabric tends to be hydrophobic, slow to absorb liquids, and generally exhibits little or no wicking of moisture. Since polyester is hydrophobic in nature, conventional wisdom would lead one to choose a hydrophilic natural fiber, such as cotton, or a hydrophilic synthetic fiber, such as nylon, as the wound contacting side of the wound care device. However, it was unexpectedly discovered that by placing a hydrophobic polyester containing surface against the wound site and a hydrophilic nylon containing surface away from the wound site, a unique one-way, directional flow of fluid away from the wound site was achieved.

The wound care device may be of any thickness, depending on the construction of the fabric. It may, however, be preferred that the thickness of the wound care device is between about 25 and about 60 mils. It may be more preferred that the wound care device is between about 35 and about 50 mils. It may be even more preferred that the wound care device is between about 38 and about 45 mils. It should be understood, and is exemplified herein, that thickness measurements may be increased when the wound care device also includes an antimicrobial finish on one or more surfaces of the wound care device.

An additional advantageous feature of the wound care device of the present invention is its ability to substantially maintain its original color, despite the presence of effective amounts of a silver-based antimicrobial agent. The elimination of color normally associated with the inclusion of silver-based antimicrobials is highly beneficial and desirable. The wound care devices (preferably, white-colored), as will be described herein, allow users thereof and their health care providers to monitor the exudates from the wound. Further, the present wound care devices exhibit long-term color stability (that is, their color does not change significantly over time while in production, transit, or storage). Finally, because the present wound care device is not discolored by the addition of the silver-based antimicrobial agent, a variety of substrate colors may be utilized or the finished wound care devices may be dyed or colored to any desired shade or hue with any type of colorant, such as, for example, pigments, dyes, tints, and the like.

Antimicrobial and Other Agents

The particular antimicrobial treatment which may be applied to the wound care device of the present invention comprises at least one silver ion-releasing compound selected from the group consisting of silver ion exchange materials (e.g. silver zirconium phosphates, silver calcium phosphates and silver zeolites), silver particles (e.g. silver metal, nanosilver, colloidal silver), silver salts (e.g. AgCl, $Ag_2CO_3$), silver glass, and mixtures thereof. One preferred silver ion-containing compound is an antimicrobial silver sodium hydrogen zirconium phosphate available from Milliken & Company of Spartanburg, S.C., sold under the tradename AlphaSan®. Other potentially preferred silver-containing antimicrobials suitable for use herein—including silver zeolites, such as a silver ion-loaded zeolite available from Sinanen Co., Ltd. of Tokyo, Japan under the tradename Zeomic®, and silver glass, such as those available from Ishizuka Glass Co., Ltd. of Japan under the tradename Ionpure®—may be utilized either in addition to, or as a substitute for, the preferred species listed above. Other silver ion-containing materials may also be used. Various combinations of these silver-containing materials may be made if adjustments to the silver release rate over time are desired.

Generally, the silver-based compound is added in an amount from about 0.01% to about 60% by total weight of the particular finish composition; more preferably, from about 0.05% to about 40%; and most preferably, from about 0.1% to about 30%. The antimicrobial finish itself, including any desired binders, wetting agents, odor absorbing agents, leveling agents, adherents, thickeners, and the like, is added to the substrate in an amount of at least about 0.01% of the total device weight.

A binder material has been found useful in preventing the antimicrobial from flaking onto the wound. Preferably, this component is a polyurethane-based binding agent, although a wide variety of cationic, anionic, and non-ionic binders may also be used, either alone or in combination. Preferably, the binding agent is biocompatible such that is does not cause negative reactions in the wound. In essence, such binders provide durability by adhering the antimicrobial to the target substrate, such as fibers or fabrics, without negatively affecting the release of silver ions to the wound.

Total add-on levels of silver to the target substrate may be 20 ppm or higher. More preferably, total add-on levels of silver may be 200 ppm or higher. Although an upper boundary limit of silver add-on levels to the target substrate has not been determined, consideration of the manufacturing economics and the potential to irritate a sensitive wound site suggests avoiding excessive silver levels.

Application of Antimicrobial and Other Agents to Substrate

Silver ion-containing compounds (such as AlphaSan®, Zeomic®, or Ionpure®) may be admixed in an aqueous dispersion with a binder to form a bath into which the target substrate is immersed. Other similar types of compounds that provide silver ions may also be utilized.

When specific polyurethane-based binder materials are utilized, the antimicrobial characteristics of the treated substrate are effective with regard to the amount of surface available silver that is released to kill bacteria, without altering the color of the treated substrate (that is, while substantially maintaining its original appearance). While it currently appears that the use of polyurethane-based binder resins are preferred due to their allowance of silver release and bio-neutral properties, in practice essentially any effective cationic, anionic, or non-ionic binder resin that is not toxic to the wound may be used.

An acceptable method of providing a durable antimicrobial silver-treated fabric surface is the application of a silver ion-containing compound and polyurethane-based binder resin from a bath mixture. This mixture of antimicrobial compound and binder resin may be applied through any technique as is known in the art, including spraying, dipping, padding, foaming, printing, and the like. By using one or more of these application techniques, a fabric may be treated with the antimicrobial compound and binder resin on only one side of the fabric (e.g. the wound contact surface of a wound care device), or it may be treated on both sides of the fabric.

The following examples further illustrate the present wound care device having fluid transfer properties, but are not to be construed as limiting the invention as defined in the claims appended hereto. All parts and percents given in these examples are by weight unless otherwise indicated.

Sample Creation and Evaluation

A. Substrate Descriptions

The fabric used for Examples 1 and 2 was a jersey knit (circular knit), multi-polymer fabric sold by Milliken & Company. The fabric was single layer of fabric comprised of approximately 66% continuous filament polyamide yarn, 19% continuous filament polyester yarn, and 15% continuous filament spandex yarn. The polyamide yarn was comprised of 2 plies of 40 denier/34 filament count nylon 6 fiber that was exposed to a texturing process prior to knitting. The polyester yarn was comprised of single ply 70 denier/34 filament count fiber that was exposed to a texturing process prior to knitting. The spandex yarn was comprised of 55 denier/3 filament count fiber.

The fabric was knitted in such as manner as to give a distinct nylon side and a distinct polyester side. The polyester side of the fabric was exposed to a face-finishing process known as sanding.

The fabric was passed through a bath containing an antimicrobial formulation (further described below) and subsequently through squeeze rollers to achieve a wet pick-up of about 85%. The fabric was then dried in a tenter frame to remove excess liquid.

B. Antimicrobial Coating Formulations

Various dispersions of an antimicrobial finish include combinations of the following components:

Antimicrobial AlphaSan® RC2000 silver-based ion exchange compound, available from Milliken & Company of Spartanburg, S.C.;

Witcobond® W-293 (67% solids) or Witcobond UCX-281F (40% solids), polyurethane binders available from Chemtura Corporation of Middlebury, Conn.; and Water.

EXAMPLE 1

The jersey knit fabric (described previously) was not treated with an antimicrobial formulation. This sample was used for Test 1 (Fluid Transport Test), Test 2 (Tensile Strength Test), Test 3 (Zone of Inhibition Test), Test 4 (Quantitative Reduction Test), Test 6 (Conductivity/Resistivity Test), and Test 7 (Thickness Test).

EXAMPLE 2

A solution was prepared according to the formulation shown below and was applied to the jersey knit fabric described previously. This sample was used for Test 1 (Fluid Transfer Test) Test 5 (Total AlphaSan® RC2000 Content Test), Test 6 (Conductivity/Resistivity Test), and Test 7 (Thickness Test).

| Formulation | |
|---|---|
| Component | Amount (pounds) |
| Water | 300.0 |
| Witcobond ® UCX-281F (polyurethane binder) | 52.9 |
| AlphaSan ® RC 2000 (antimicrobial agent, 10% Ag) | 95.3 |

EXAMPLE 3

A solution was prepared according to the formulation shown below and was applied to the jersey knit fabric described previously. This sample was used for Test 2 (Tensile Strength Test), Test 3 (Zone of Inhibition Test), Test 4 (Quantitative Reduction Test), and Test 5 (Total AlphaSan® RC2000 Content Test).

| Formulation | |
|---|---|
| Component | Amount (pounds) |
| Water | 328.0 |
| Witcobond ® 293 (polyurethane binder) | 28.0 |
| AlphaSan ® RC 2000 (antimicrobial agent, 10% Ag) | 94.0 |

Each of Examples 2 and 3, when applied to the jersey knit fabric, result in a wound care device comprising approximately 16% polyester fiber, 53% nylon fiber, 12% spandex fiber, 15% antimicrobial agent, and 4% binding agent.

C. Comparative Sample Descriptions

Several commercially available silver-containing wound care devices were also purchased for evaluation. These textile-based wound care devices are notated as Comparative Examples A-L below and include a wide variety of wound dressing combinations.

COMPARATIVE EXAMPLE 1—"Actisorb® 220", a multi-component nonwoven wound care device comprised of a highly porous, silver impregnated charcoal cloth sandwiched between two nylon nonwoven layers containing 220 mg of silver; available from Johnson & Johnson of Somerville, N.J.

COMPARATIVE EXAMPLE 2—"Acticoat® 5", a three layered wound care device consisting of three layers—a layer of polyethylene film, a middle layer of rayon/polyester blend nonwoven fabric, and a second layer of film; nano-crystalline silver particles are deposited onto the film layers; available from Smith and Nephew of Largo, Fla.

COMPARATIVE EXAMPLE 3—"Acticoat® 7", a five-layered wound care device consisting of an inner sheet of polyethylene film treated with nano-crystalline silver sandwiched between two layers of untreated rayon fabric; this composite structure is further sandwiched between two layers of polyethylene film treated with nano-crystalline silver; available from Smith and Nephew of Largo, Fla.

COMPARATIVE EXAMPLE 4—"Silverlon®", a silver-plated nylon fabric; available from Argentum Medical, LLC of Lakemont, Ga.

COMPARATIVE EXAMPLE 5—"Aquacel®", a hydrofiber dressing; available from Convatec, a Bristol-Myers-Squibb Company of England.

COMPARATIVE EXAMPLE 6—"Aquacel® Ag", a silver-impregnated sodium carboxymethyl cellulose hydrofiber having 1.2% silver; available from Convatec, a Bristol-Myers-Squibb Company of England.

COMPARATIVE EXAMPLE 7—"Lyofoam®", a sterile, non-adherent, absorbent dressing; available from Convatec, a Bristol-Myers-Squibb Company of England.

COMPARATIVE EXAMPLE 8—"Foam Dressing", a non-adherent foam; available from 3M of St. Paul, Minn.

COMPARATIVE EXAMPLE 9—"Woven Gauze Pad", a medical dressing manufactured for Dynarex Corporation of Orangeburg, N.Y.

COMPARATIVE EXAMPLE 10—"Mirasorb™ Gauze", a nonwoven gauze; available from Ethicon, Inc., a division of Johnson & Johnson of Somerville, N.J.

COMPARATIVE EXAMPLE 11—"Evolon®", a nonwoven fabric comprised of multi-component fibers; the multi-component fibers are comprised of individual nylon and polyester fibers that have been longitudinally split into their individual components by hydroentanglement; the fabric is described in U.S. Pat. Nos. 5,899,785 and 5,970,583 both of which are assigned to Firma Carl Freudenberg of Weinheim, Germany and which are incorporated entirely herein by reference.

COMPARATIVE EXAMPLE 12—"Versalon™", nonwoven medical sponges; available from Kendall and trademark of Tyco Healthcare Group LP.

COMPARATIVE EXAMPLE 13—"Contreet® F", a polyurethane foam having AlphaSan® RC2000 silver throughout the polymer matrix; available from Coloplast A/S.

D. Example Testing and Evaluation

Each of the above examples was tested for a variety of characteristics as will be described below. Further, commercially available products (referred to as Comparative Examples A-E and described above) were also tested for comparison with the present antimicrobial wound care substrates. The testing procedures will be described in detail as follows. However, a listing of the tests used is found below.

| Test 1. | Fluid Transport Test (Internally developed method) |
| Test 2. | Tensile Strength Test (ASTM D 5034) |
| Test 3. | Zone of Inhibition Test (Kirby-Bauer Agar Diffusion Assay) |
| Test 4. | Quantitative Reduction Test (Modified AATCC Method 100) |
| Test 5 | Total AlphaSan ® RC 2000 Content Test (Ashing Technique) |
| Test 6 | Conductivity/Resistivity Test (AATCC Test Method 76) |
| Test 7 | Thickness Test (ASTM D 1777-96) |

Test 1: Fluid Transport Test

The purpose of this test is to measure the amount of fluid that is transported from the wound contact side of the wound care device (Side A) to the non-wound contact side of the device (Side B). The test also attempts to measure the amount of fluid pushed back to the wound contact side of the device (Side A).

Simulated wound fluid ("SWF") was prepared by adding 16.60 g NaCl and 0.56 g CaCl$_2$ to a 2 L volumetric flask. The flask was then filled to volume (2000 mL total) with deionized water. The flask was then capped and shaken until all of the salts were completely dissolved. The simulated wound fluid is comprised of 0.142M (142 mM) NaCl (aq) and 0.0025M (2.5 mM) CaCl$_2$ (aq).

A test sample of a wound care device (5 cm in diameter) was placed onto a polypropylene disc (5 cm in diameter). Twenty drops of simulated wound fluid was added to Side A of the test sample using a dropper. The test sample was allowed to rest in a horizontal position for 2 minutes. The test sample was then sandwiched in a vertical position between two discs of filter paper (Whitman filter paper 3, diameter=110 mm) using a clamp—Filter Paper A contacted Side A of the test sample and Filter Paper B contacted Side B of the test sample. The test sample was held in this position for 5 seconds. It was determined that the clamp exerts a pressure of 340 mm Hg.

Filter papers A and B had been weighed prior to the test. They were then weighed after the test and difference in weight was determined. This weight difference provides a calculation of the amount of SWF transferred from the wound care device to Filter Paper A and/or B.

The SWF was added to the polyester side ("Side A") of the wound care device of the present invention. SWF was added to the wound contact side of competitive dressings, as directed by the product brochures.

Test results are shown in Table 1. The values are provided as "percent weight change." The percent weight change represents the weight of the fluid absorbed relative to the dry weight of the filter paper. It is calculated by subtracting the weight of the dry filter paper (grams) from the weight of the wet filter paper (grams) and dividing this difference by the weight of the dry filter paper. This value is then multiplied by 100. The average percent weight change for Side A and Side B for each Example and Comparative Example was also determined and is provided in Table 1 as well. For instance, the percent weight change values for Side A and Side B for Example 1A, 1B, and 1C were averaged together. The results are shown as 4.8% and 24.2%, respectively. The standard deviation of the average value is also provided.

TABLE 1

Fluid Transport Properties of Inventive and Comparative Wound Care Devices (Provided As Percent Weight Change)

| Sample | Side A Fluid | Side B fluid | Average Side A fluid | Standard Deviation | Average Side B fluid | Standard Deviation |
|---|---|---|---|---|---|---|
| Example 1A (no antimicrobial agent) | 4.1% | 23.4% | 4.8% | 0.7% | 24.2% | 0.8% |
| Example 1B | 5.3 | 24.3 | | | | |
| Example 1C | 5.1 | 25.0 | | | | |
| Example 2A (AlphaSan ® RC 2000) | 8.2 | 17.8 | 9.8 | 1.8 | 18.4 | 0.5 |
| Example 2B | 9.3 | 18.8 | | | | 0 |
| Example 2C | 11.8 | 18.6 | | | | |
| Comp. Ex. 3A (Acticoat ® 7) | 21.8 | 8.1 | 24.6 | 3.0 | 11.4 | 3.1 |
| Comp. Ex. 3B | 27.7 | 14.0 | | | | |
| Comp. Ex. 3C | 24.4 | 12.2 | | | | |
| Comp. Ex. 4A (Silverlon ®) | 5.5 | 6.0 | 6.2 | 0.6 | 2.2 | 3.3 |
| Comp. Ex. 4B | 6.8 | 0.1 | | | | |
| Comp. Ex. 4C | 6.3 | 0.7 | | | | |
| Comp. Ex. 5A (Aquacel ®) | 1.6 | 0.0 | 1.3 | 0.4 | 0.0 | 0.0 |
| Comp. Ex. 5B | 1.5 | 0.0 | | | | |
| Comp. Ex. 5C | 0.9 | 0.0 | | | | |
| Comp. Ex. 6A (Aquacel ® Ag) | 2.6 | 2.0 | 2.3 | 0.2 | 1.8 | 0.2 |
| Comp. Ex. 6B | 2.2 | 1.5 | | | | |
| Comp. Ex. 6C | 2.1 | 1.8 | | | | |
| Comp. Ex. 7A (Lyofoam ®) | 23.2 | 12.7 | 27.3 | 3.9 | 10.2 | 2.5 |
| Comp. Ex. 7B | 30.9 | 10.0 | | | | |
| Comp. Ex. 7C | 27.9 | 7.8 | | | | |
| Comp. Ex. 8A (Foam Dressing) | 20.5 | 0.0 | 22.9 | 2.2 | 0.0 | 0.0 |
| Comp. Ex. 8B | 23.6 | 0.1 | | | | 0 |
| Comp. Ex. 8C | 24.7 | 0.1 | | | | |

TABLE 1-continued

Fluid Transport Properties of Inventive and Comparative
Wound Care Devices (Provided As Percent Weight Change)

| Sample | Side A Fluid | Side B fluid | Average Side A fluid | Standard Deviation | Average Side B fluid | Standard Deviation |
|---|---|---|---|---|---|---|
| Comp. Ex. 9A (Woven Gauze Pad) | 18.1 | 17.8 | 19.4 | 2.2 | 16.5 | 1.4 |
| Comp. Ex. 9B | 18.2 | 16.6 | | | | |
| Comp. Ex. 9C | 21.9 | 15.1 | | | | |
| Comp. Ex. 10A (Mirasorb ™ Gauze) | 31.0 | 1.6 | 29.4 | 2.1 | 2.3 | 1.0 |
| Comp. Ex. 10B | 27.0 | 1.8 | | | | |
| Comp. Ex. 10C | 30.1 | 3.5 | | | | |
| Comp. Ex. 11A (Evolon ®) | 14.0 | 11.6 | 13.0 | 1.4 | 12.2 | 2.0 |
| Comp. Ex. 11B | 13.6 | 10.6 | | | | |
| Comp. Ex. 11C | 11.4 | 14.5 | | | | |
| Comp. Ex. 13A (Contreet ® F) | 18.8 | 0.0 | 18.3 | 0.7 | 0.0 | 0.0 |
| Comp. Ex. 13B | 17.6 | 0.0 | | | | |
| Comp. Ex. 13C | 18.5 | 0.0 | | | | |

The results shown in Table 1 demonstrate that the inventive wound care device provide significant movement of fluid away from the wound contact side of the device (Side A) to the reservoir side of the device (Side B). This directional fluid movement occurs even under pressure exerted from both sides of the wound care device. The results further show that the fluid movement is generally uni-directional in that the reservoir side (Side B) collects and holds most of the fluid and keeps it from flowing back to the wound contact side of the device (Side A). These features are exhibited by the inventive device whether or not the device also contains an antimicrobial agent.

It was also noted during this test that both of the Aquacel® wound care devices fell apart. They were not able to hold together structurally after absorbing the SWF.

Test 2: Tensile Strength

Tensile strength (grab) of various wound care devices was determined using ASTM D 5034. The purpose of this test is to determine structural integrity of wet and dry wound care devices. The devices were wetted by dipping them in simulated wound fluid (same formulation as described previously). The test results are provided in Table 2. Measurements are shown in pounds of force (lbf). Higher values indicate that more force was needed to tear the sample.

TABLE 2

Tensile Strength of Inventive and Comparative Wound Care Devices

| Sample ID sample | Sample Condition Dry/Wet | Average of All Peaks (lbf) Mean | Average of All Peaks (lbf) Standard Deviation |
|---|---|---|---|
| Example 1 (no antimicrobial agent) | Dry | 3.848 | 0.004 |
| Example 1 (no antimicrobial agent) | Wet | 5.106 | 0.216 |
| Example 3 (AlphaSan ® RC 2000) | Dry | 3.827 | 0.357 |
| Example 3 (AlphaSan ® RC 2000) | Wet | 4.561 | 0.300 |
| Comparative Example 5 (Aquacel ®) | Dry | 3.089 | 0.130 |

TABLE 2-continued

Tensile Strength of Inventive and Comparative Wound Care Devices

| Sample ID sample | Sample Condition Dry/Wet | Average of All Peaks (lbf) Mean | Average of All Peaks (lbf) Standard Deviation |
|---|---|---|---|
| Comparative Example 5 (Aquacel ®) | Wet | Sample fell apart when wetted. Test was not done. | Sample fell apart when wetted. Test was not done. |
| Comparative Example 7 (Lyofoam ®) | Dry | 1.163 | 0.012 |
| Comparative Example 7 (Lyofoam ®) | Wet | 1.013 | 0.014 |
| Comparative Example 12 (Versalon ™) | Dry | 0.563 | 0.030 |
| Comparative Example 12 (Versalon ™) | Wet | 0.595 | 0.133 |

Test 3: Zone of Inhibition Test

Zone of Inhibition testing was conducted to determine the antimicrobial activity of various wound care devices against several microbes using a modified version of the Kirby-Bauer Susceptibility Test. A brief description of the test method is included below. A full description of the test method may be found in the following document: National Committee for Clinical Laboratory Studies (NCCLS) M2-A8: Performance Standards for Antimicrobial Disk Susceptibility Tests; Approved Standard—Eighth Edition; 2003.

Several Gram-positive and Gram-negative bacteria as well as fungi (yeast) were chosen to illustrate the antimicrobial efficacy of the inventive wound care device. Gram-positive bacteria include, for example and without limitation, *Staphylococcus aureus, Clostridium perfringens, Enterococcus faecium* and *Bacillus cereus*. Gram-negative bacteria include, for example and without limitation, *Klebsiella pneumoniae, Escherichia coli, Acinetobacter baumannii, Enterobacter cloacae, Proteus mirabilis,* and *Pseudomonas aeruginosa*. Fungi, such as yeast, include for example, *Candida albicans* and *Saccharomyces cerevisiae*. Many of these organisms were selected to demonstrate the antimicrobial efficacy of the Examples below. However, it should be understood to be within the scope of this invention that similar results would be obtained against other bacteria and fungi.

An overnight culture of the test microbe was diluted into saline (0.85% NaCl) to a concentration of $10^6$ cells/ml. Petri dishes containing Diagnostic Sensitivity Test (DST) Agar were inoculated with 0.25 ml of the cell suspension and incubated for 1 hour. A sample (15 mm diameter circle) of each wound care device was then placed at the center of the agar plate. The agar plate was incubated for 24 hours at 37° C. After measuring the extent of the zones (in mm), the samples were transferred to a fresh DST plate inoculated with the same microbe. The process was repeated for three days (total).

The results of the zone of inhibition tests for each sample are shown in Table 3.

Samples (about 40 mm in diameter) were placed in sterile 60 ml plastic jars and exposed to bacteria (0.4 ml of $10^5$ cells/ml) suspended in (a) simulated wound fluid (prepared as previously described) and 2% Bovine Serum Albumin and (b) simulated wound fluid (prepared as previously described) and 20% Bovine Serum. The jars were tightly capped and incubated for 22 hours at 37° C. The 0.4 ml volume was determined to completely wet the wound dressing samples without excess fluid in the container. Example 3 was inoculated on the polyester side of the wound care device. After incubation for 24 hours at 37° C., the samples were covered with 10 ml of Tryptic Soy Broth with surfactants and cysteine to deactivate any residual silver and vortexed to remove attached cells. The number of viable cells in the wash solution was quantified using a microtiter plate-based "Most-Probable Number"

TABLE 3

Zones of Inhibition for Inventive and Comparative Wound Care Devices

| | Zone of Inhibition (mm) | | | | | | | | |
|---|---|---|---|---|---|---|---|---|---|
| | Example 3 (AlphaSan® RC 2000) | | | Comparative Example 3 (Acticoat® 7) | | | Comparative Example 4 (Silverlon®) | | |
| Microbe (ATCC#) | Day 1 | Day 2 | Day 3 | Day 1 | Day 2 | Day 3 | Day 1 | Day 2 | Day 3 |
| *Acinetobacter baumannii* (#19606) | 5.5 | 5 | 4 | 6 | 5 | 4 | 5.5 | 3.5 | 0.5 |
| *Enterobacter cloacae* (#13047) | 1.5 | 1 | 1 | 1 | 1 | 0.5 | 1 | 1 | 0 |
| *Enterococcus faecalis* (#51299) (VRE) | 3.5 | 2.5 | 1.5 | 4.5 | 3 | 2 | 3.5 | 2.5 | 1.5 |
| *Enterococcus faecium* (#19434) | 5.5 | 3.5 | 6 | 5.5 | 3.5 | 6 | 6 | 2 | 4.5 |
| *Escherichia coli* (#10536) | 4.5 | 4 | 2 | 4.5 | 4 | 2.5 | 4 | 2 | 0 |
| *Escherichia coli* (#8739) | 5 | 4.5 | 3 | nd | nd | nd | nd | nd | nd |
| *Klebsiella pneumoniae* (#4352) | 5.5 | 3 | 3 | 4.5 | 3.5 | 3 | 5 | 2 | 0 |
| *Proteus mirabilis* (#25933) | 5 | 2 | 0 | 4 | 2.5 | 2 | 3.5 | 0 | 0 |
| *Proteus vulgaris* (#8427) | 3.5 | 3 | 2.5 | 3 | 3 | 3 | 2.5 | 1 | 0 |
| *Staphylococcus aureus* (#6538) | 6 | 5 | 3 | 5 | 5 | 4 | 5 | 5 | 4 |
| *Staphylococcus aureus* (#43300) (MRSA) | 4.5 | 3 | 2.5 | 3.5 | 2.5 | 2.5 | 4 | 2.5 | 2.5 |
| *Staphylococcus epidermidis* (#12228) | 8 | 4 | 3.5 | 7 | 4 | 4 | 7 | 2 | 1 |
| *Staphylococcus epidermidis* (#51625) (MRSE) | 7.3 | 5.5 | 4.5 | 7 | 6.5 | 5 | 7 | 6 | 4.5 |
| *Candida albicans* (#10231) | 6 | 4 | 4 | 7 | 4 | 4 | 6 | 2 | 0 |
| *Saccharomyces cerevisiae* (#9763) | 4 | 5 | 5.5 | 4 | 4 | 1.5 | 3 | 1.5 | 0 | nd = not determined

The test results in Table 3 illustrate that the inventive wound care device (Example 3) exhibits considerable efficacy against several types of Gram-positive and Gram-negative bacteria, as well as against various fungi (yeast). Example 1 (no antimicrobial treatment) did not exhibit any efficacy (data not shown).

Test 4: Quantitative Reduction

Antimicrobial efficacy against *Staphylococcus aureus* ATCC #6538 was measured for the inventive wound care device and several competitive wound care devices. The quantitative reduction of bacteria after exposure to the treated samples versus untreated fabric was assessed using a modified version of AATCC Method 100-1999, "Antibacterial Finishes on Textile Materials Assessment of."

assay. The level of viable cells recovered from the treated samples was compared to the number of cells recovered from untreated fabric and the percent reduction calculated. The results are shown in Table 4.

TABLE 4

Percent Reduction of Inventive and Comparative Wound Care Devices Compared to Untreated Fabric Against *Staphylococcus aureus*

| Sample ID | Percent Reduction of *S. aureus* (SWF and 2% Bovine Serum Albumin) | Percent Reduction of *S. aureus* (SWF and 20% Bovine Serum) |
|---|---|---|
| Example 1 (no antimicrobial agent) | 0.00 | 0.00 |

TABLE 4-continued

Percent Reduction of Inventive and Comparative Wound Care Devices Compared to Untreated Fabric Against *Staphylococcus aureus*

| Sample ID | Percent Reduction of S. aureus (SWF and 2% Bovine Serum Albumin) | Percent Reduction of S. aureus (SWF and 20% Bovine Serum) |
|---|---|---|
| Example 3 (AlphaSan ® RC 2000) | 99.96 | 99.75 |
| Comparative Example 3 (Acticoat ® 7) | 99.99 | 99.99 |
| Comparative Example 13 (Contreet ® F) | 94.13 | 99.69 |

The results in Table 4 indicate that over 99% of viable bacteria were reduced after 24 hours of contact with the inventive wound care device (Example 3) compared to similar fabric without the antimicrobial treatment (Example 1). For this testing, *Staphylococcus aureus* was selected as the representative microbe. However, it should be understood to be within the scope of this invention that Example 3 would exhibit similar antimicrobial efficacy against other Gram-positive and Gram-negative bacteria and against fungi such as *C. albicans*.

Test 5: Total AlphaSan® Content

Total ALPHASAN® Content Test

The amount of AlphaSan® antimicrobial incorporated into or onto an article can be determined by measurement of elements unique to the antimicrobial compound. For AlphaSan® antimicrobial, the two elements of highest abundance are silver or zirconium. Because zirconium is more abundant in the AlphaSan® antimicrobial product and is easier to measure, it is preferable to use zirconium as the signature element for determining the level of AlphaSan® antimicrobial in an article. The amount of AlphaSan® antimicrobial incorporated into or onto the wound care device of Examples 2 and 3 was determined using the following ashing technique.

A sample of fabric (weighing approximately 1 gram but with weight measured to four significant digits) was placed in a clean, dry ceramic crucible which had been weighed. The crucible containing the fabric sample was placed in a muffle furnace whose temperature ramped up at 3° C./minute to 750° C. The temperature was then held at 750° C. for four hours. The system was then cooled and the crucible transferred to a desiccator in which it was allowed to reach an equilibrium temperature. The crucible was then weighed. This provides the percent solids of inorganic constituents.

The fabric sample was then ground in the ceramic crucible to obtain a uniform sample. Approximately 0.05 g weight (again measured to four significant digits) was then taken from the ceramic crucible and placed in a platinum crucible. Four milliliters of 50% $HNO_3$, followed by 15-20 drops of 48% HF, were added to the crucible. The crucible was heated over a hot plate until the sample completely dissolved. The sample solution was then transferred to a 100 mL volumetric flask.

The crucible was then rinsed with 5% $HNO_3$, with the rinse solution being added to the flask. The solution was diluted to the 100 mL mark with 5% $HNO_3$. The dilute solution was transferred to a polyethylene storage container. Analysis for the desired active ingredient (in this case, zirconium) was performed using an Inductively Coupled Plasma Optical Emission Spectrometer device (e.g., a Perkin Elmer Optima 4300DV). Calculations are apparent to one skilled in the art. The amount of AlphaSan® RC2000 present on the wound care device is provided as a weight percent based on the weight of the fabric. The results are shown in Table 5.

TABLE 5

Total AlphaSan ® RC2000 Content of Inventive Wound Care Device

| Sample ID | Percent AlphaSan ® RC2000 |
|---|---|
| Example 2 | 16 |
| Example 3 | 17 |

Test 6: Conductivity/Resistivity Test

The purpose of this test is to determine the conductivity and resistivity (R) of the inventive wound care device. The test was performed according to AATCC Test Method 76.

The test results are shown in Table 6. Each value is an average of four measurements. Log R also includes the standard deviation.

TABLE 6

Conductivity and Resistivity of Inventive Wound Care Device

| Sample ID | Conductivity (amperes) | Resistivity (ohms/sq.) | Log R (ohms/sq.) |
|---|---|---|---|
| Example 1 (no antimicrobial) | 4.204E−11 | 2.147E+12 | 12.33 +/− 0.06 |
| Example 2 (AlphaSan ® RC 2000) | 3.958E−11 | 2.238E+12 | 12.34 +/− 0.07 |

The detection range of the testing equipment is in the range of 12-13 for the Log R value. Both Example 1 and Example 2 are below the detection limit of the testing equipment. Thus, the inventive wound care device is non-electrically conductive.

Test 7: Thickness Test

The purpose of this test was to measure the thickness of the inventive wound care device. The test was performed according to ASTM D 1777-96. The results are provided as an average with the standard deviation of ten measurements for each sample. The results are shown in Table 7.

TABLE 7

Thickness of Inventive Wound Care Device

| Sample ID | Average Thickness (mils) |
|---|---|
| Example 1 (no antimicrobial) | 40.75 +/− 0.40 |
| Example 2 (AlphaSan ® RC 2000) | 42.20 +/− 0.25 |

As described previously, any of the substrates described herein may be used to form the wound care device of the present invention. Alternatively, one or more of these substrates may be joined together in any possible combination to form a composite, multi-layered, wound care device. The layers may be joined together through various techniques such as ultrasonic welding, heat or pressure lamination, the use of adhesives, needle punching, hydraulic needling, sewing, or other fiber and/or fabric layer laminating or joining processes known to those skilled in the art. The layers may be joined together only at intermittent locations or the layers may be joined together completely.

The topical antimicrobial finish of the current invention may be applied to any one or more of the substrate layers comprising the composite wound care device. Additionally, an odor absorbing agent or layer may be included on or within one or more layers of the composite wound care device. Furthermore, in some instances, the wound care device may have an adhesive layer so that the device may be held in place over the wound site. In such cases, a layer of removable film may be placed over the wound-facing side of the wound care device to protect the adhesive layer until ready for use. Alternatively, the wound care device may be held in place by wrapping long pieces of wound dressing, such as gauze, over and around the wound care device and securing the free end in place by any suitable means, such as tape, adhesive, pins, clips, or hooks.

Thus, the above description and examples show that a topical antimicrobial finish may be applied to a variety of substrates to achieve an antimicrobially effective, silver-containing wound care device having the desired characteristics of antimicrobial efficacy, functional release of silver, and absence of a dark color. As has been described herein, the present wound care device possesses a significant advantage over competitive products, in that it exhibits a white color uncharacteristic of silver-containing antimicrobial articles and in that the white color is sustainable over long periods (i.e., in production, transit, and storage).

These and other modifications and variations to the present invention may be practiced by those of ordinary skill in the art, without departing from the spirit and scope of the present invention. Furthermore, those of ordinary skill in the art will appreciate that the foregoing description is by way of example only, and is not intended to limit the scope of the invention described in the appended claims.

We claim:

1. A method for managing moisture at a wound site comprising the steps of:
   (a) providing a wound care device comprising: a fabric having a wound contact surface and a wound fluid reservoir surface, wherein said wound contact surface is comprised primarily of hydrophobic fiber and said fluid reservoir surface is comprised primarily of hydrophilic fiber, wherein said hydrophobic and hydrophilic fibers are intermeshed together in a jersey knit construction, and wherein said wound care device transports wound fluid uni-directionally from said wound contact surface to said wound fluid reservoir surface upon exposure to a wound;
   (b) placing said wound contact surface of said wound care device in contact with said wound site; and
   (c) allowing said wound care device to transport wound fluid uni-directionally from said wound contact surface to said wound fluid reservoir surface.

2. The method of claim 1, wherein said wound contact surface is coated with a composition comprising at least one silver ion-containing compound.

* * * * *